United States Patent
Polak

(10) Patent No.: US 6,383,767 B1
(45) Date of Patent: May 7, 2002

(54) LUMINESCENT IN VIVO GLUCOSE MEASUREMENT

(75) Inventor: Anthony J. Polak, Lake Zurich, IL (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/489,372

(22) Filed: Jan. 21, 2000

(51) Int. Cl.⁷ .................................................. C12Q 1/54
(52) U.S. Cl. ...................................... 435/14; 422/82.06
(58) Field of Search ........................ 435/14; 422/82.06; 424/9.1, 9.8, 425; 436/172; 600/342

(56) References Cited

U.S. PATENT DOCUMENTS

| | | | |
|---|---|---|---|
| 5,342,789 A | * 8/1994 | Chick et al. ................ | 436/501 |
| 5,990,479 A | 11/1999 | Weiss et al. ................ | 250/307 |
| 6,040,194 A | * 3/2000 | Chick et al. ................ | 436/501 |
| 6,081,736 A | * 6/2000 | Colvin et al. ............... | 600/377 |
| 6,134,461 A | * 10/2000 | Say et al. .................... | 600/345 |
| 6,163,714 A | * 12/2000 | Stanley et al. .............. | 600/316 |

* cited by examiner

Primary Examiner—Ralph Gitomer

(57) ABSTRACT

A luminescent in vivo glucose measurement method and apparatus is provided. The luminescent in vivo glucose measurement method includes the steps of illuminating displaced luminescent molecules with illuminating light, the displaced luminescent molecules and associated captive glucose analogue molecules being contained within an implanted luminescent in vivo measurement apparatus implanted within the interstitial fluid of the subject, and measuring an emitted light, the emitted light being emitted in response to the illumination, wherein the emitted light is related to the glucose level in the interstitial fluid.

24 Claims, 2 Drawing Sheets

LUMINESCENT IN VIVO GLUCOSE MEASUREMENT

BACKGROUND OF THE INVENTION

1. Field of the Invention

The present invention relates generally to a luminescent in vivo glucose measurement, and more particularly to a luminescent in vivo glucose measurement using quantum dots.

2. Description of the Background Art

Measurement of body chemistry components is an essential part of modern health care. By measuring individual body chemistry components of a subject animal or human, such as a subject's blood chemistry, specific health characteristics of the subject can be determined.

One such body chemistry component is glucose (blood sugar) level. The glucose level in a subject may be analyzed and tracked for a number of reasons, but especially for monitoring diseases such as diabetes. Control of glucose levels in diabetic subjects is know to minimize diabetes side effects and to prolong the life of the subject.

In the related art, glucose testing and monitoring may be performed in different ways. First, it may be done in vitro (in an artificial environment) by extracting and testing blood specimens. This is undesirable for a variety of reasons, including pain and discomfort, invasiveness, inconvenience, time required, and the provision of an unfortunate avenue for infection.

The second method is in vivo (i.e., in the body) method of glucose measurement. As the name implies, the measurement may be performed through the skin of the subject, and may be non-invasive in nature. This has been done in the related art by illuminating a blood vessel of the subject through the subject's skin and measuring the energy that is absorbed or scattered in the subject's bloodstream. This has advantages of non-invasiveness, quickness, and ease of use. However, it suffers from drawbacks in accuracy, as the results may depend on and be affected by other bloodstream components, blood vessel depth, skin characteristics, etc.

In another related art blood specimen testing and measurement method, the detection of glucose or blood sugar may be aided by the use of an organic luminescent dye. The related art organic luminescent dye, such as FITC (fluorescein), is capable of covalently bonding to a glucose containing molecule. After the related art luminescent dye has bonded to a glucose analogue which competes with glucose to bind to a substrate, it is illuminated with a light source, causing it to emit photons. The photon emission can be measured and correlated to an amount of glucose present in the sample. Detection and measurement of light emission may therefore yield an emitted light level substantially proportional to the blood sugar level of the subject's blood.

However, related art dyes are organic in nature, and suffer from several drawbacks. First, related art organic luminescent dyes suffer from decomposition, wherein the bond between the dye and the sugar weakens over time. This means that the test or measurement must be taken within a fairly restrictive time window in order to be acceptably accurate. As a result, the related art organic luminescent dye cannot be used for extended periods as is desired for in vivo measurements, and is suitable only for in vitro laboratory use.

Second, related art organic luminescent dyes suffer from photo-bleaching, wherein the illuminating light breaks bonds within the dye, resulting in a decrease in luminescence over time. Repeated illumination therefore weakens the luminescent effect.

A third drawback is that related art organic luminescent dyes have fairly broad emission spectra (i.e., they fluoresce across a relatively broad range of light wavelengths, often overlapping within the excitation wavelength). The emission spectra is a characteristic of the related art organic luminescent dye, and cannot be adjusted to have desired emission and absorption properties. In addition, skin is most transparent to light having a red or near infrared wavelength, but the related art organic luminescent dye produces a bright green luminescence (typically of a wavelength of about 520 nanometers).

There remains a need in the art, therefore, for an improved in vivo blood glucose measurement.

SUMMARY OF THE INVENTION

A luminescent in vivo glucose measurement method for measuring a glucose level in an interstitial fluid of a subject is provided according to a first aspect of the invention. The method comprises the steps of illuminating displaced luminescent molecules with illuminating light, the displaced luminescent molecules and associated captive glucose analogue molecules being contained within an implanted luminescent in vivo measurement apparatus implanted within the interstitial fluid of the subject, and measuring an emitted light, the emitted light being emitted in response to the illumination, wherein the emitted light is related to the glucose level in the interstitial fluid.

A luminescent in vivo glucose measurement apparatus for measuring a glucose level in an interstitial fluid of a subject is provided according to a second aspect of the invention. The apparatus comprises a container having an interior region and at least one surface region formed of a semi-permeable membrane that allows glucose to pass through, the container also having an illumination region wherein light may enter the container, an agglutinating layer on at least one interior surface region and apart from the illumination region, a plurality of captive glucose analogue molecules in the interior region, with a captive sugar of the plurality of captive glucose analogue molecules capable of reversibly attaching to the agglutinating layer, and a plurality of luminescent molecules in the interior region, with a luminescent molecule of the plurality of luminescent molecules being hydrophilic and being bonded to at least one associated captive glucose analogue molecule of the plurality of captive glucose analogue molecules, wherein when a glucose molecule of the subject passes through the at least one surface region formed of a semi-permeable membrane and attaches to the agglutinating layer, a displaced luminescent molecule and an associated captive glucose analogue molecule travels to the illumination region of the container, and wherein illumination of all displaced luminescent molecules and the associated captive glucose analogue molecules through the illumination region produces a luminescence that is related to the glucose level of the interstitial fluid.

A luminescent in vivo glucose measurement compound is provided according to a third aspect of the invention. The compound comprises a quantum dot having a core and a shell, the core selected from the group consisting of indium arsenide, indium nitride, indium phosphide, zinc tellurium, gallium arsenide, gallium antimony, indium antimony, and lead sulfide, and the shell selected from the group consisting of indium phosphide, indium nitride, cadmium sulfide, zinc selenide, zinc sulfide, and lead selenide, at least one captive glucose analogue molecule, and at least one binding molecule that is hydrophilic and is capable of bonding to the at least one captive glucose analogue molecule and to the quantum dot, wherein the quantum dot is capable of absorbing light and emitting light as a result of the absorbing.

The above and other features and advantages of the present invention will be further understood from the following description of the preferred embodiments thereof, taken in conjunction with the accompanying drawings.

DETAILED DESCRIPTION OF THE PREFERRED EMBODIMENTS

Figure 1:
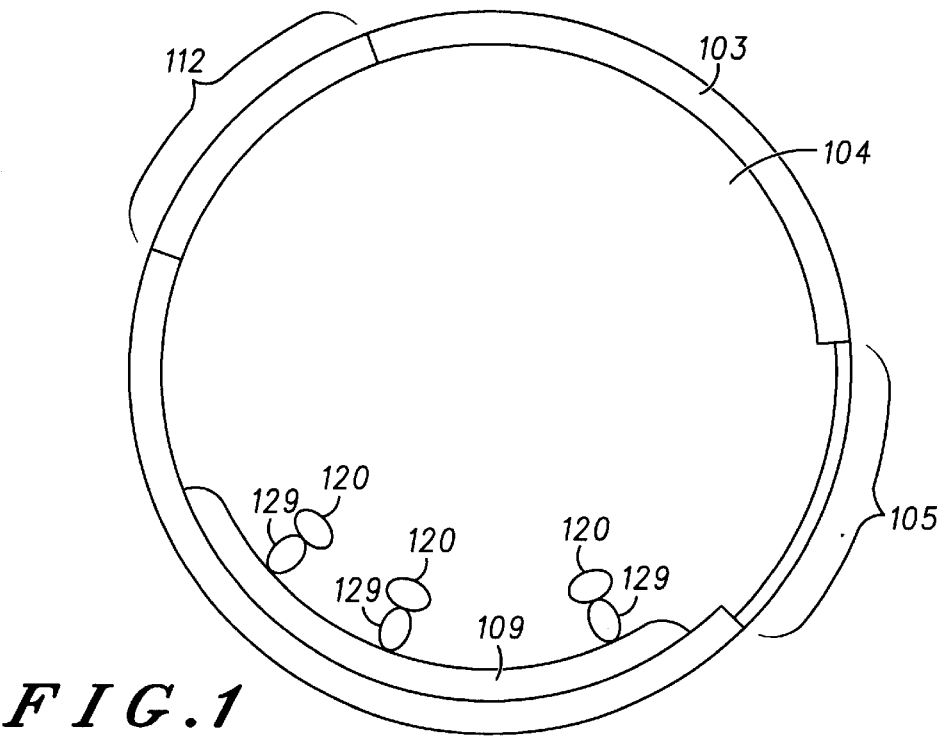
FIG. 1 shows detail of one embodiment of the apparatus.

In one embodiment of a luminescent in vivo glucose measurement method of the present invention, the method is used to determine a subject's blood glucose measurement by determining a glucose level present in an interstitial fluid of the subject (the fluid surrounding cells). In a lesser preferred embodiment, the present invention may be used to measure a blood glucose level in a bloodstream of the subject.

In a first step, an implanted luminescent in vivo glucose measurement apparatus is illuminated by a light source. The luminescent in vivo glucose measurement apparatus is implanted into the interstitial fluid of the subject and illuminated therein. Although the apparatus may be implanted anywhere on the subject, it is preferred that the apparatus be implanted in an area that is convenient for obtaining a reading. Preferably, the apparatus is implanted in a wrist region of a human subject, and is preferably implanted at a depth of about three to four millimeters below the outer surface of the subject's skin. Although the apparatus may obtain a faster reading when implanted in a blood vessel, clotting or blockage may potentially be encountered. For this reason, implantation in the interstitial fluid is preferred.

Because the apparatus employs a luminescent material (that may be inorganic), the apparatus may be repeatably used to measure a subject's glucose level. Therefore, the luminescent in vivo glucose measurement apparatus is designed to be implanted for a period of at least one to five years.

Because the apparatus is fairly close to the surface, the illuminating light reaches it. However, not all wavelengths of light are preferred, as the light source should transmit light that travels well through skin. Infrared light (non-visible light having wavelengths in the range of 750 to 2,000 nanometers) is capable of passing through skin with relatively low absorption. Therefore, it is preferred that infrared light be used, and it is further preferred that near infrared light having a wavelength of about 830 nanometers to about 1200 nanometers be used. In a lesser preferred embodiment, visible light may be used to illuminate the implanted apparatus.

In a second step, as a result of the illumination, the contents of the implanted apparatus emits light. A portion of the emitted light emerges from the skin of the subject and may be detected and measured. The amount of emitted light from the apparatus is related to the amount of glucose in the interstitial fluid. Therefore, the blood glucose level may be reliably and conveniently determined by measuring the interstitial glucose level.

The glucose level of the interstitial fluid is related to the glucose level of the subject's bloodstream, although there is a short time interval before changes in a blood glucose level are reflected in the interstitial glucose level. The emitted light output may be proportional to the glucose level, although the emitted light level may need to be adjusted or correlated by use of a table, a constant(s), or a calibration function in order to accurately quantify the glucose level. Alternatively, a fluorescent reference dye may be used. The reference dye is included in the apparatus and always fluoresces when illuminated. The reference dye therefore provides an expected light emission level that can be used to calibrate the measurement by compensating for the implant depth of the apparatus.

The emitted light may be of the same wavelength as the illuminating light, but is preferably of a separate and distinct wavelength so that a detection device may easily discriminate between the illuminating light and the emitted light, and so that the detection device may easily eliminate any illuminating light that was reflected or scattered. In a preferred embodiment, the emitted light is red shifted by at least 30 nanometers from the illuminating light, allowing use of filters to reject any "background noise" light.

In addition, the illumination and detection steps are preferably done simultaneously. Because the emitted light has a wavelength (or wavelength band) that is distinct from the wavelength (or wavelength band) of the illuminating light, the emitted light can be detected and measured while the illuminating is being done. The advantage of this is that no wait period is needed between illumination and detection, eliminating the need for precise and expensive time measurement and synchronization equipment. Based on the quantity of emitted light, a detecting device may determine the interstitial glucose level and therefore the blood glucose level.

FIG. 1 shows detail of one embodiment of a luminescent in vivo glucose measurement apparatus. The apparatus includes a container 103 having an inner region 104, an agglutinating layer 109, and luminescent molecules 120 and associated captive glucose analogue molecules 129. The inner region 104 may be filled with the luminescent molecules 120 and associated captive glucose analogue molecules 129 and a solvent or carrier liquid, such as, for example, water or interstitial fluid. Alternatively, the luminescent molecules 120 may be in a colloidal form.

The shape and physical dimensions of the container 103 may vary as desired. In the present embodiment the container 103 is a cylinder of a diameter less than about one millimeter, or a disk less than about four millimeters in diameter. A small container 103 greatly eases the task of implanting the device and makes it less noticeable to the subject.

The illumination region 112 is a light transparent region and is only a partial region of the container 103. The illumination region 112 allows light to enter and leave the container 103.

The agglutinating layer 109 is formed on at least one interior surface region of the container 103, and may cover regions of various sizes, as desired. The agglutinating layer 109 is formed apart from the illumination region 112, so that when the apparatus is illuminated, the illuminating light "I" does not impinge on the agglutinating layer 109.

The material of the agglutinating layer 109 has an affinity for sugar molecules. In the preferred embodiment, the agglutinating layer 109 is lectin and more preferably is concanavalin A. Because of the sugar affinity of the agglutinating layer 109, any sugar molecules within the inner region 104 tend to attach to the agglutinating layer 109 through a reversible competitive bonding, although they can also detach. Reversible competitive bonding means that a sugar molecule may bond to the agglutinating layer 109 and then detach on its own, with multiple sugar molecules competing for locations at which to bond. Statistically, sugar molecules within the inner region 104 tend to be attached to the agglutinating layer 109 as opposed to drifting in the inner region 104.

Captive glucose analogue molecules 129 are included in the apparatus as sugar analogues that have the same basic properties as glucose. However, the captive glucose analogue molecules 129 cannot escape the container 103. Captive glucose analogue molecules 129 are contemplated to be sugar analogues such as polysaccharides having glucose units. Dextran is one such sugar analogue consisting of D-glucose linked α-glycosidically, primarily in 1,6 bonds, but with some 1,3 and 1,4. The choice of a sugar analogue is mainly determined by molecular weight, as discussed below.

The container 103 must have at least one semi-permeable membrane region 105 that allows a subject's glucose to pass through into the inner region 104. The semi-permeable membrane 105 may be a small portion of the container 103, or alternatively the entire container 103 may be formed of the semi-permeable membrane region 105, such as, for example, a dialysis tube. The openings in the semi-permeable membrane region 105 are such that the subject's glucose can pass through the semi-permeable membrane region 105 and into the container 103, but the captive glucose analogue molecules 129 within the apparatus cannot escape. For this reason, dextran is a preferred captive glucose analogue molecule 129, having a molecular weight of 70,000 daltons, as opposed to a molecular weight cut-off characteristic of a typical dialysis tube of about 10,000 daltons.

The luminescent molecules 120 (discussed in detail below in conjunction with FIGS. 3A and 3B) are present in the inner region 104 for the sole purpose of being displaced by glucose of the subject. When implanted and when no glucose of the subject is present, the quantity of luminescent molecules 120 and associated captive glucose analogue molecules 129 is adequate to substantially attach to and cover the agglutinating layer 109 without a substantial excess.

It should be noted that not all of the luminescent molecules 120 and associated captive glucose analogue molecules 129 may be attached to the agglutinating layer 109 at any given time. Captive glucose analogue molecules 129 may attach and detach repeatedly, and a small quantity may be drifting freely at any time. These free captive glucose analogue molecules 129 and associated luminescent molecules 120 may appear as "background noise" when the container 103 is illuminated. This background noise is expected and may be compensated for in the measurement process.

Figure 2:
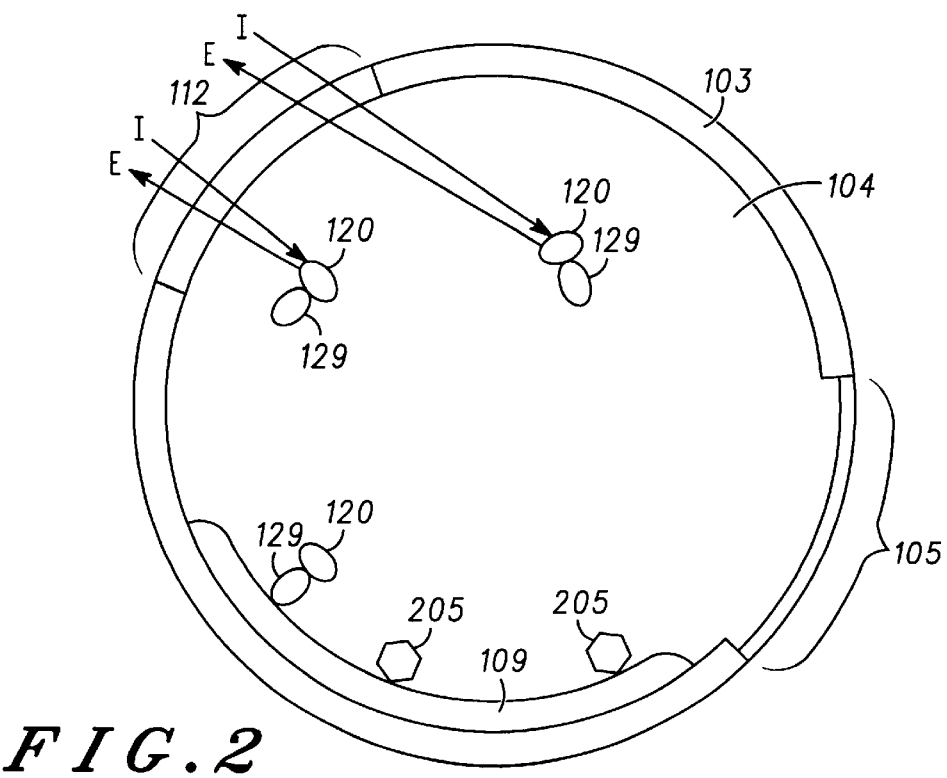
FIG. 2 shows the apparatus when implanted, illustrating the displacing action upon which the glucose measurement is based.

FIG. 2 shows the apparatus when implanted, illustrating the displacing action upon which the glucose measurement is based. When a subject's glucose 205 enters the inner region 104 by passing through the semi-permeable membrane region 105, the subject's glucose 205 may stick to the agglutinating layer 109. Correspondingly, a proportional amount of luminescent molecules 120 and associated captive glucose analogue molecules 129 are displaced from the agglutinating layer 109 to drift in the inner region 104. Illuminating light "I" may enter the inner region 104 through the illumination region 112 and may therefore impinge on displaced luminescent molecules 120 and associated captive glucose analogue molecules 129. As a result, the drifting luminescent molecules 120 may be induced to emit light, with emitted light "E" leaving the apparatus through the illumination region 112 or other appropriate region. The amount of emitted light "E" from the displaced luminescent molecules 120 may then be detected and measured.

Figure 3A:
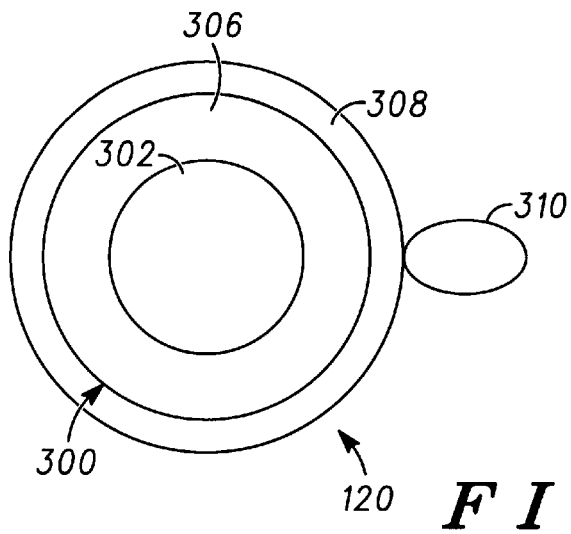
FIG. 3A shows a first embodiment of a luminescent molecule.

FIG. 3A shows a first embodiment of the luminescent molecule 120. The luminescent molecule 120 includes a quantum dot 300, a hydrophilic coating 308, and may include at least one bi-functional linker molecule 310, depending on the characteristics of the hydrophilic coating 308. The hydrophilic coating 308 may also serve as the bifunctional linker molecule 310. The bi-functional linker molecule 310 may be used to bond a sugar to the hydrophilic coating 308 (which is in turn bonded to the quantum dot 300).

The quantum dot 300 is formed of inorganic compounds, as opposed to related art luminescent dyes, which are generally organic in nature and tend over time to weaken, decompose, or break free from target molecules. The quantum dot 300 is formed of two or more layers of semiconductor or metallic elements, with the luminescent property of the quantum dot 300 arising from quantum-size confinement due to an extremely small size. Each quantum dot 300 preferably has a diameter in the 5 to 80 nanometer range.

The characteristics of a quantum dot 300 may be determined by both the physical size and the elemental composition of the quantum dot portion of the luminescent molecule 120. This allows the light absorption characteristic and the luminescent light emission characteristic to be tuned to a narrow wavelength band. For example, in the preferred embodiment, the quantum dot 300 may absorb light of about 830 nanometers and may luminescently emit light at about 900 nanometers.

The quantum dot 300 has a core 302 and a shell 306. Examples of compounds for use in the core 302 are indium arsenide, indium nitride, indium phosphide, zinc tellurium, gallium arsenide, gallium antimony, indium antimony, and lead sulfide.

Examples of compounds for use in the shell 306 are indium phosphide, indium nitride, cadmium sulfide, zinc selenide, zinc sulfide, and lead selenide.

Examples of quantum dot composition are an indium arsenide core and an indium phosphide shell, an indium arsenide core and a cadmium sulfide shell, an indium arsenide cor and a zinc selenide shell, and a lead sulfide core and a lead selenide shell. Of course, other compositions and combinations may be used so long as they have suitable light absorption and emission properties.

Because of the metallic/semiconductor composition of the quantum dot 300, it is not water soluble. In order to overcome this drawback, the quantum dot 300 is preferably given an organic or inorganic hydrophilic coating 308. For instance, surfactants or lipid bilayers are examples of a class of organic compounds that will make the quantum dot hydrophilic, and silica ($SiO_2$) is an example of an inorganic material that will make the quantum dot hydrophilic. The hydrophilic coating 308 is preferably a silicon dioxide or hydrophilic organic layer plus a bi-functional linker molecule 310. The hydrophilic organic layer may also serve as the bi-functional linker molecule 310. Examples of the bi-functional linker molecule 310 include but are not limited to thiols, mercaptocarboxylic acids (such as mercaptoacetic acid, for example)or cyanides. The bi-functional linker molecule 310 bonds to an individual captive sugar 129 (see FIG. 1) and also to the hydrophilic coating 308.

Figure 3B:
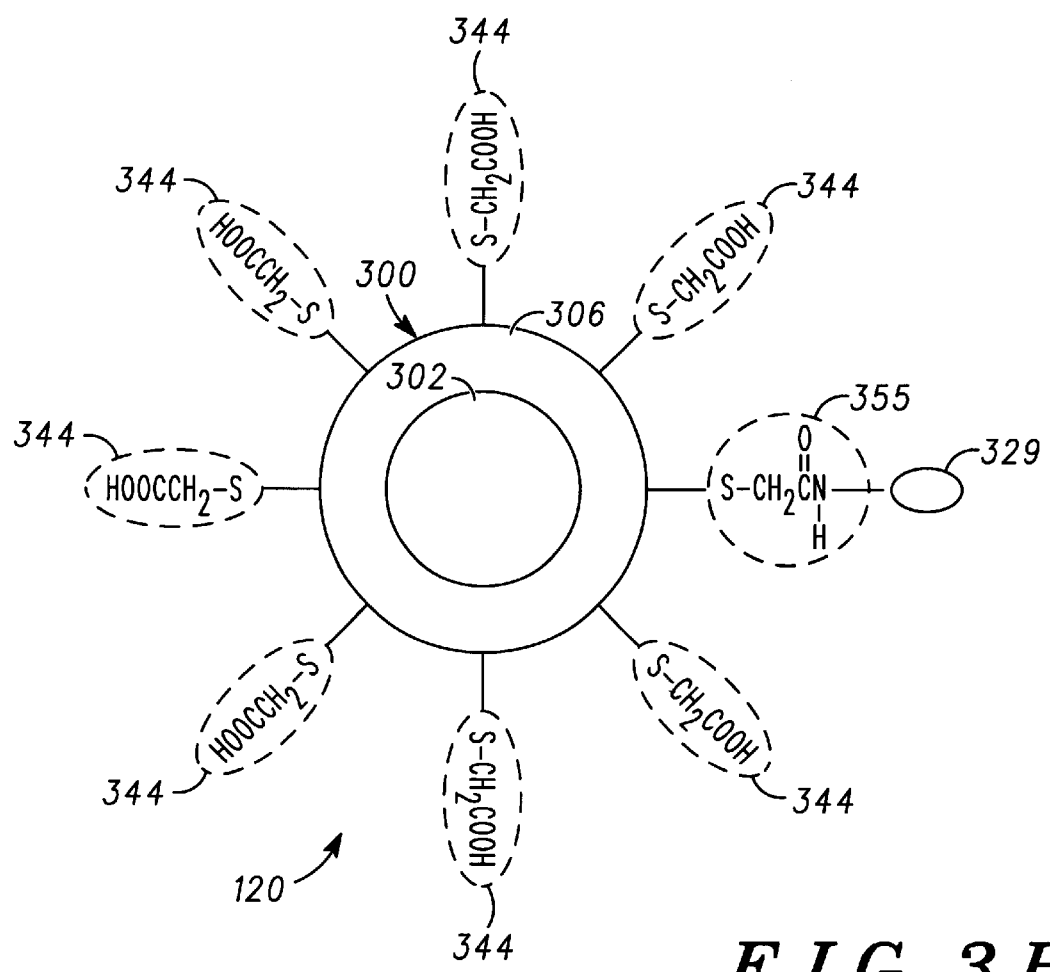
FIG. 3B shows mercaptoacetic acid molecules bonded to a quantum dot.

FIG. 3B shows the use of a mercaptoacetic acid 344 as a quantum dot coating, wherein multiple mercaptoacetic acid molecules 344 may bind to the quantum dot 300. When using mercaptoacetic acid 344 as the hydrophilic layer 308, a bi-functional linker molecule 310 is not needed. This is because, as shown by the bonded mercaptoacetic acid molecule 355, the mercapto group attaches to the quantum dot 300, while the acetic acid group binds to the captive sugar 129. The bond to the sugar may be an amide bond, such as shown in FIG. 3B, or may be an ester bond.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A luminescent in vivo glucose measurement method for measuring a glucose level in an interstitial fluid of a subject, comprising the steps of:
   displacing luminescent molecules and associated captive glucose analogue molecules into an illumination region;
       illuminating said displaced luminescent molecules within said illumination region with illuminating light, said displaced luminescent molecules and associated captive glucose analogue molecules being contained within an implanted luminescent in vivo measurement apparatus implanted within said interstitial fluid of said subject; and
   measuring an emitted light, said emitted light being emitted in response to said illumination;
       wherein said emitted light is related to said glucose level in said interstitial fluid.

2. The luminescent in vivo glucose measurement method of claim 1, wherein said glucose level in said interstitial fluid is substantially equal to a blood glucose level.

3. The luminescent in vivo glucose measurement method of claim 1, wherein said method is used to measure a glucose level in a bloodstream of said subject.

4. The luminescent in vivo glucose measurement method of claim 1, wherein said displaced luminescent molecules are inorganic.

5. The luminescent in vivo glucose measurement method of claim 1, wherein said emitted light is correlated to a interstitial glucose level.

6. The luminescent in vivo glucose measurement method of claim 1, wherein said luminescent in vivo measurement apparatus is implanted about three to about four millimeters below an outer surface of a patient's skin.

7. The luminescent in vivo glucose measurement method of claim 1, wherein said illuminating light is of a first wavelength and said emitted light is of a second wavelength.

8. The luminescent in vivo glucose measurement method of claim 1, wherein said illuminating light is an infrared light.

9. The luminescent in vivo glucose measurement method of claim 1, wherein a wavelength of said illuminating light is in a range of about 800 nanometers to about 2000 nanometers.

10. The luminescent in vivo glucose measurement method of claim 1, wherein a wavelength of said illuminating light is about 830 nanometers and a wavelength of said emitted light is about 900 nanometers.

11. The luminescent in vivo glucose measurement method of claim 1, wherein said illuminating light travels from outside said subject, through said subject's skin, and into said luminescent in vivo measurement apparatus.

12. The luminescent in vivo glucose measurement method of claim 1, wherein said emitted light travels from said luminescent in vivo measurement apparatus, through said subject's skin, and to a region outside said subject.

13. A luminescent in vivo glucose measurement method for measuring a glucose level in an interstitial fluid of a subject, comprising the steps of:
   (a) providing an implanted luminescent in vivo measurement apparatus within said interstitial fluid, said implanted luminescent in vivo measurement apparatus comprising a container having an interior region, an illumination region wherein light may enter said interior region, an agglutinating layer on at least one surface of said interior region and apart from said illumination region, and luminescent molecules and associated captive glucose analogue molecules reversibly attached to said agglutinating layer;
   (b) providing a means of allowing glucose from the subject to enter said interior region, said glucose causing said luminescent molecules and associated captive glucose analogue to become displaced from said agglutinating layer and into said illumination region;
   (c) illuminating displaced luminescent molecules within said illumination region; and
   (d) measuring an emitted light from said displaced luminescent molecules, said emitted light being emitted in response to said illumination;
       wherein said emitted light is related to said glucose level in said interstitial fluid.

14. The luminescent in vivo glucose measurement method of claim 13, wherein said glucose level in said interstitial fluid is substantially equal to a blood glucose level.

15. The luminescent in vivo glucose measurement method of claim 13, wherein said method is used to measure a glucose level in a bloodstream of said subject.

16. The luminescent in vivo glucose measurement method of claim 13, wherein said displaced luminescent molecules are inorganic.

17. The luminescent in vivo glucose measurement method of claim 13, wherein said emitted light is correlated to a interstitial glucose level.

18. The luminescent in vivo glucose measurement method of claim 13, wherein said luminescent in vivo measurement apparatus is implanted about three to about four millimeters below an outer surface of a patient's skin.

19. The luminescent in vivo glucose measurement method of claim 13, wherein said illuminating light is of a first wavelength and said emitted light is of a second wavelength.

20. The luminescent in vivo glucose measurement method of claim 13, wherein said illuminating light is an infrared light.

21. The luminescent in vivo glucose measurement method of claim 13, wherein a wavelength of said illuminating light is in a range of about 800 nanometers to about 2000 nanometers.

22. The luminescent in vivo glucose measurement method of claim 13, wherein a wavelength of said illuminating light is about 830 nanometers and a wavelength of said emitted light to about 900 nanometers.

23. The luminescent in vivo glucose measurement method of claim 13, wherein said illuminating light travels from outside said subject, through said subject's skin, and into said luminescent in vivo measurement apparatus.

24. The luminescent in vivo glucose measurement method of claim 13, wherein said emitted light travels from said luminescent in vivo measurement apparatus, through said subject's skin, and to a region outside said subject.

* * * * *